DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JULY 28, 1970

876 O.G. 815

T876,002
PREPARATION OF LIGHT-COLOR OLEFIN SULFONATES

John Thomas Wilfrid Smith, North Shields, Northumberland, England, assignor to The Procter & Gamble Company, Cincinnati, Ohio, a corporation of Ohio

Filed Aug. 6, 1969, Ser. No. 848,096
Int. Cl. C07c *143/16*
U.S. Cl. 260—513
No Drawing. 7 Pages Specification

Color development during sulfonation of olefins with sulfur trioxide can be markedly reduced by pretreating the olefins with a low molar proportion of sulfur trioxide diluted with inert gas; contacting the pretreated olefins with an adsorbent to remove color bodies; separating the treated olefins from the adsorbent; and then proceeding with sulfur-trioxide sulfonation in a conventional manner. Bleaching the product olefin sulfonate with chlorine or peroxygen bleach is optional to improve color still further. Preferred conditions are a falling film reactor, pretreatment sulfur trioxide usage below ten mol percent based on the olefins, and silica gel or fuller's earth as adsorbent. Contact with the adsorbent can be accomplished by mixing the adsorbent with the pretreated olefin followed by filtration, or more conveniently by passing the pretreated olefin through a column of the adsorbent. The process is especially applicable to straight chain alpha olefins containing ten to twenty carbon atoms; particularly those derived from cracked petroleum waxes but also including those prepared by buildup of short chain olefins.